United States Patent
Papadopoulou et al.

(10) Patent No.: US 7,618,986 B2
(45) Date of Patent: Nov. 17, 2009

(54) METHOD OF TREATING LATENT TUBERCULOSIS

(75) Inventors: Maria V. Papadopoulou, Skokie, IL (US); William D. Bloomer, Winnetka, IL (US)

(73) Assignee: Evanston Northwestern Healthcare, Evanston, IL (US)

( * ) Notice: Subject to any disclaimer, the term of this patent is extended or adjusted under 35 U.S.C. 154(b) by 0 days.

(21) Appl. No.: 11/843,764

(22) Filed: Aug. 23, 2007

(65) Prior Publication Data

US 2008/0076797 A1 Mar. 27, 2008

Related U.S. Application Data

(60) Provisional application No. 60/841,701, filed on Sep. 1, 2006.

(51) Int. Cl.
*A61K 31/473* (2006.01)
*A61P 31/06* (2006.01)

(52) U.S. Cl. .................................................. 514/313
(58) Field of Classification Search ................ None
See application file for complete search history.

(56) References Cited

U.S. PATENT DOCUMENTS

| 5,294,715 | A | 3/1994 | Papadopoulou-Rosenzweig et al. |
| 5,602,142 | A | 2/1997 | Papadopoulou-Rosenzweig et al. |
| 5,958,947 | A | 9/1999 | Papadopoulou-Rosenzweig et al. |

OTHER PUBLICATIONS

Barry et al., Current Pharmaceutical Design, 10:3239-3262, 2004.*

* cited by examiner

*Primary Examiner*—Brian-Yong S Kwon
*Assistant Examiner*—Bong-Sook Baek
(74) *Attorney, Agent, or Firm*—Marshall, Gerstein & Borun LLP

(57) ABSTRACT

2-Nitroimidazolyl-alkylaminoquinolines, and compositions containing the same, useful in the treatment of tuberculosis are disclosed. Methods of treating tuberculosis using the 2-nitroimidazolyl-alkylaminoquinolines, and compositions containing the same, also are disclosed.

9 Claims, 1 Drawing Sheet

METHOD OF TREATING LATENT TUBERCULOSIS

CROSS-REFERENCE TO RELATED APPLICATION

This application claims the benefit of U.S. provisional patent application No. 60/841,701, filed Sep. 1, 2006.

FIELD OF THE INVENTION

The present invention relates to methods of treating tuberculosis. More particularly, the present invention relates to a method of treating latent tuberculosis comprising administrating a therapeutically-effective amount of a 2-nitroimidazolyl-alkylaminoquinoline to an individual in need thereof.

BACKGROUND OF THE INVENTION

Tuberculosis (TB) is an infectious disease that typically attacks the lungs, but is capable of attacking most parts of the body. Tuberculosis is caused by *Mycobacterium tuberculosis*, and is spread from person to person through the air. When individuals infected with TB cough, laugh, sneeze, sing, or talk, TB bacteria can be spread. If a second person inhales TB bacteria, a possibility exists that the second person also will become infected with tuberculosis. However, repeated contact typically is required for infection.

TB is a primary public health threat, and is an increasing worldwide problem, especially in Africa. TB is the single leading cause of death from an infectious disease worldwide, and it is estimated that, worldwide, one third of the population is infected with latent TB, over 150 million people will contract active TB, and about 36 million people will die over the next 20 years unless TB control is improved. Medical experts estimate that about 10 million Americans are infected with TB bacteria, and about 10 percent of these individuals will develop active TB in their lifetime. Furthermore, HIV and TB form a lethal combination, with each condition speeding the progress of the other condition.

Except for very young children, few individuals become sick immediately after tuberculosis bacteria enter the body. Many tuberculosis bacteria that enter the lungs are immediately killed by the body's immune system. TB bacteria that survive are captured inside white blood cells called macrophages. The captured bacteria can remain alive inside these cells in a dormant state for many years (latent TB). In 90 to 95% of cases, the TB bacteria cause no further problems. But in about 5 to 10% of infected people, the TB bacteria begin to multiply (active TB). It is in this active TB phase that an infected person actually becomes sick and can spread the disease.

Typically, activation of latent TB bacteria occurs within the first two years of infection, but activation may not occur for a very long time. The mechanism by which dormant bacteria becomes active is not precisely known, but activation often occurs when the immune system becomes impaired, for example, from advanced age, the use of corticosteroids, or HIV infection. Like many infectious diseases, tuberculosis spreads more quickly and is much more dangerous in individuals having a weakened immune system. For such individuals, including the very young, the very old, and those who are also infected with HIV, tuberculosis can be life threatening.

Presently-used drugs to treat TB were developed more than 40 years ago. Treatments using these drugs are very long and require an excessive number of doses, e.g., up to eight pills a day for longer than six months. The drug isoniazid is an effective anti-TB drug. Isoniazid (termed "INH") is administered daily for 6 to 9 months. Shorter latent TB treatments use rifampin plus pyrazinamide daily for 2 months, or rifampin alone daily for 4 months. Such burdensome treatments increase patient noncompliance and can lead to an increase in multidrug-resistant tuberculosis (MDR TB). In addition, the presently-used drugs typically do not target latent, nonproliferating TB bacteria.

An individual infected with TB, but not suffering from TB disease, i.e., has latent TB, can be administered preventive therapy, which kills bacteria in order to prevent a case of active TB. An individual with a positive tuberculin skin test who becomes infected with HIV has a high risk of developing an active TB infection. Similarly, an individual who takes corticosteroids has a greatly increased risk of activating latent tuberculosis. Such individuals need a treatment for latent tuberculosis. An important aspect of TB prevention, therefore, is treating individuals diagnosed with latent TB.

If an individual has active TB, the individual typically is administered a combination of several drugs. It is very important, however, that the individual continue a correct treatment regimen for the full length of the treatment. If the drugs are taken incorrectly, or treatment is stopped, the individual can suffer a relapse and will be able to infect others with TB.

When an individual becomes sick with TB a second time, the TB infection may be more difficult to treat because the TB bacteria have become drug resistant, i.e., TB bacteria in the body are unaffected by some drugs used to treat TB. In particular, some TB bacteria become resistant to the effects of various anti-TB drugs, and these multidrug resistant TB bacteria then can cause MDR TB disease. MDR TB is a very dangerous form of tuberculosis, and like regular TB, MDR TB can be spread to other individuals.

To help avoid drug resistance in the treatment of TB, a four-drug regimen, i.e., isoniazid, rifampin, pyrazinamide, and streptomycin, is administered to TB patients. Aminoglycosides, such as streptomycin, are important anti-TB agents, but their utility is restricted by the requirement of parenteral administration, which is inconvenient and leads to poor patient compliance. It is theorized that poor patient compliance also can lead to the development of drug resistance, and it appears that the frequency of streptomycin resistance among anti-TB drugs is surpassed only by isoniazid.

In view of the above, an urgent need exists for new, effective anti-TB agents that are useful in a treatment regimen for both active and latent TB, and that effectively treat TB caused by multidrug resistant (MDR) strains of bacteria. Therefore, it would be advantageous to provide compounds and compositions for administration to an individual in the treatment of TB, and particularly latent TB. As set forth in detail hereafter, the present invention is directed to the use of 2-nitroimidazolyl-alkylaminoquinolines, and pharmaceutical compositions containing the same, for use in methods of treating tuberculosis, and particularly latent tuberculosis.

Compounds termed nitroimidazopyrans (NAPs) have been reported as having activity against known forms of TB (Stover et al., *Nature*, 405, 962-966, (2000)). One particular NAP is termed PA-824, having a structure

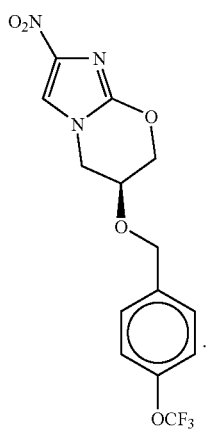

PA-824 is specific against *M. tuberculosis*. The NAPs perform differently from current anti-TB drugs because they are activated by reduction, rather than oxidation.

Another compound reported as being useful against latent TB bacteria is metronidazole (Edwards, *Antimicrob. Chemother.*, 5, 499-502 (1999)) having a structure

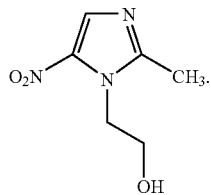

Additional compounds useful in the treatment of latent TB would be an important advance in the art.

SUMMARY OF THE INVENTION

The present invention is directed to a method of treating tuberculosis (TB). More particularly, the present invention is directed to methods of treating latent, active, and multidrug-resistant TB by administering a therapeutically-effective amount of a 2-nitroimidazolyl-alkylaminoquinoline to a mammal in need thereof. Preferably, the 2-nitroimidazolyl-alkylaminoquinoline is capable of weakly intercalating DNA.

Accordingly, one aspect of the present invention is to provide a method of treating TB in a mammal, including humans. The present invention is particularly effective in a method of preventing an active TB infection by treating a latent TB infection.

Another aspect of the present invention is to provide a pharmaceutical composition comprising a 2-nitroimidazolyl-alkylaminoquinoline, or salt thereof, that can be administered to an individual in a therapeutically-effective amount to treat latent, active, or multidrug-resistant TB.

Another aspect of the present invention is to provide a method of treating TB comprising administering a pharmaceutical composition comprising (a) a 2-nitroimidazolyl-alkylaminoquinoline and, optionally, (b) one or more additional drugs useful in the treatment of TB to a mammal in need thereof.

Still another aspect of the present invention is to provide an article of manufacture comprising:

(a) a packaged pharmaceutical composition comprising a 2-nitroimidazolyl-alkylaminoquinoline;

(b) an insert providing instructions for the administration of the 2-nitroimidazolyl-alkylaminoquinoline; and (c) a container for (a) and (b).

Yet another aspect of the present invention is to provide an article of manufacture comprising:

(a) a packaged pharmaceutical composition comprising a 2-nitroimidazolyl-alkylaminoquinoline;

(b) a packaged pharmaceutical composition comprising a second therapeutic agent useful in a treatment of tuberculosis;

(c) an insert providing instructions for a simultaneous or sequential administration of (a) and (b) to treat tuberculosis; and (d) a container for (a), (b), and (c).

Still another aspect of the present invention is to provide a method of treating tuberculosis comprising administration of a therapeutically-effective amount of a 2-nitroimidazolyl-alkylaminoquinoline to an individual in need thereof, wherein the 2-nitroimidazolyl-alkylaminoquinoline operates under hypoxic conditions and preferably is hydrophilic.

Another aspect of the present invention is to provide a method of treating tuberculosis comprising administrating a therapeutically-effective amount of a 2-nitroimidazolyl-alkylaminoquinoline having a general structural formula (I) or (II), or a pharmaceutically acceptable salt thereof, to an individual in need thereof,

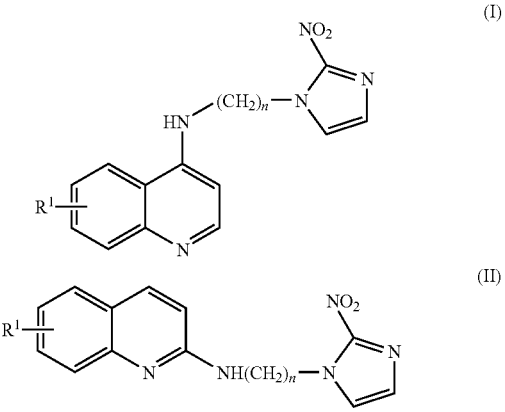

wherein $R^1$ is present at the 6, 7, or 8 ring position of the quinoline ring and is selected from the group consisting of halo, methyl, methoxy, and trifluoromethyl, and n is an integer 2 through 6. The compounds of structural formulae (I) and (II) are effective in treating latent TB, and also can be used in methods of treating active TB and MDR TB.

Yet another aspect of the present invention is to provide a method of treating tuberculosis comprising administration of a therapeutically-effective amount of a 2-nitroimidazolyl-alkylaminoquinoline termed NLCQ-1, NLCQ-2, a pharmaceutically acceptable salt of either compound, or a mixture of the compounds, to an individual in need thereof.

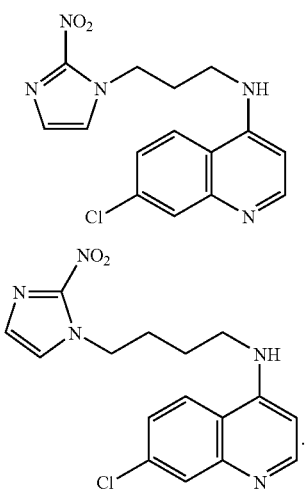

NLCQ-1

NLCQ-2

These and other aspects and advantages of the present invention will become apparent from the following detailed description of the preferred embodiments.

DETAILED DESCRIPTION OF THE PREFERRED EMBODIMENTS

Figure 1:
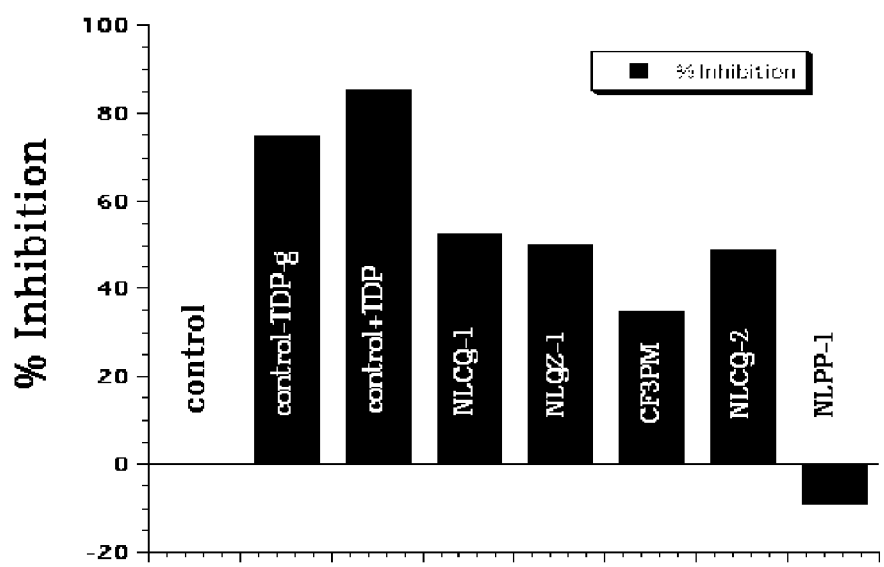
FIG. 1 contains bar graphs of % inhibition showing the ability of various compounds to inhibit a TB enzymatic system that assists in forming an essential TB cell wall component.

As previously discussed, an important link in the effort to retard or eliminate the spread of TB infections is the treatment of latent TB prior to its activation to active TB. The treatment of latent TB has been hindered by a lack of active drugs, and burdensome and lengthy treatment methods, which lead to a reduced patient compliance and an increase in MDR TB.

The current treatment for TB is a combination therapy using the drugs isoniazid (INH), pyrazinamide (PZA), streptomycin (SM), rifampin (RIF, rifamycins), and ethambutol (EMB). Of these drugs, only RIF is used to treat latent TB. Other anti-TB drugs are in development or clinical trials, such as moxifloxacin and PA-824, as are nitroimidazole analogs, carboxylates, quinolones, macrolides, InhA inhibitors, isocitrate lyase inhibitors, pleuromutilins, and nitroimidazole-oxazoles (e.g., OPC-87683). These drugs target TB bacteria at different sites, e.g., DNA gyrase, cell wall synthesis, ribosomes, and fatty acid metabolism. Some drugs, like PA-824 and the nitroimidazoles, form reactive species which target multiple sites in the TB bacterium.

The present invention is directed to compounds and methods useful in the treatment of latent TB, and which exhibit one or more of the following benefits: (1) helping control or eradicate TB by targeting latent TB, (2) shortening the duration of the anti-TB treatment, e.g., to less than three months, such as one to two months, (3) demonstrating activity against MDR TB, and (4) providing an anti-TB drug therapy that is compatible with HIV therapies.

In accordance with an important feature of the present invention, a class of compounds termed 2-nitroimidazolyl-alkylaminoquinolines has been found to be capable of treating latent TB. The 2-nitroimidazolyl-alkylaminoquinolines and related compounds are disclosed in U.S. Pat. Nos. 5,602,142; and 5,958,947, each incorporated herein by reference in its entirety. The 2-nitroimidazolyl-alkylaminoquinolines have an ability to weakly intercalate DNA and operate under hypoxic conditions. The 2-nitroimidazolyl-alkylaminoquinolines preferably are hydrophilic compounds, i.e., having a water solubility of at least 2 mM, preferably at least 4 mM, and more preferably at least 5 mM, in distilled water, and are stable for at least one month in aqueous solution at 5° C.

Preferred 2-nitroimidazolyl-alkylaminoquinolines are hydrophilic. Most preferred 2-nitroimidazolyl-alkylaminoquinolines have a general structural formula (I) or (II), or a pharmaceutically acceptable salt thereof,

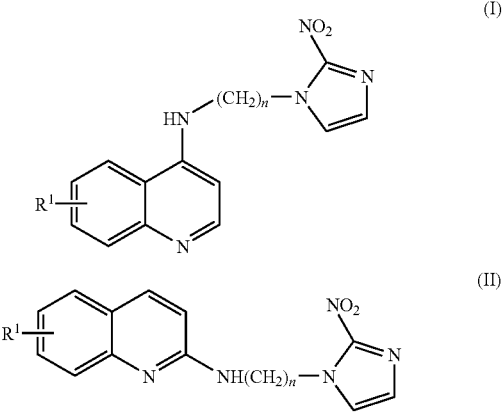

wherein $R^1$ is present at the 6, 7, or 8 ring position of the quinoline ring and is selected from the group consisting of halo, methyl, methoxy, and trifluoromethyl, and n is an integer 2 through 6.

The numbering of the quinoline ring system is as follows:

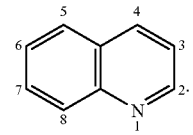

Especially preferred 2-nitroimidazolyl-alkylaminoquinolines are termed NLCQ-1 and NLCQ-2, which have the following structural formulae:

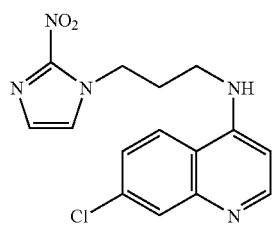

NLCQ-1

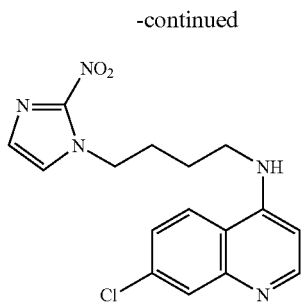

NLCQ-2 or a pharmaceutically acceptable salt thereof.

4-[3-(2-Nitro-1-imidazolyl)-propylamino]-7-chloro-quinoline hydrochloride (NLCQ-1) and 4-[4-(2-nitro-1-imidazolyl)-butylamino]-7-chloroquinoline hydrochloride (NLCQ-2) were originally developed as DNA-targeted bioreductive prodrugs against cancer to show that weak DNA-intercalation provides sufficiently high DNA-affinity to produce toxicity, yet is sufficiently low to permit efficient extravascular diffusion and penetration to hypoxic tumor tissue.

From prior studies with NLCQ-1 and NLCQ-2, it was shown that these compounds are activated by reductive enzymes (cytochrome P450 reductase and $b_5$ reductase) to toxic metabolites that can damage or kill cells only under a hypoxic environment, thus demonstrating hypoxic selectivities of 12-388 in various murine or human cancer cells (*Oncol Res* 12:185-192, (2000) and *Oncol Res* 14: 21-29, (2003)).

It is known that nitroimidazole-based compounds, such as metronidazole and the nitroimidazopyran PA-824, show activity against *M. tuberculosis* (MTB) upon reductive activation (*Nature* 405:962, (2000)). In the literature it is also known that nitroheterocycles are activated by *E. Coli* B nitroreductase, which is hypothesized to be a key enzyme present in the tuberculosis bacteria.

The synthesis of 2-nitroimidazolyl-alkylaminoquinolines is disclosed in U.S. Pat. Nos. 5,602,142 and 5,958,947, each incorporated herein by reference. NLCQ-1 and NLCQ-2 were prepared as follows.

NLCQ-1 was synthesized as outlined in the scheme below.

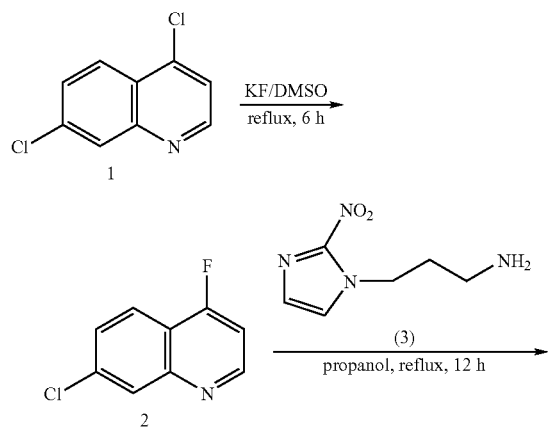

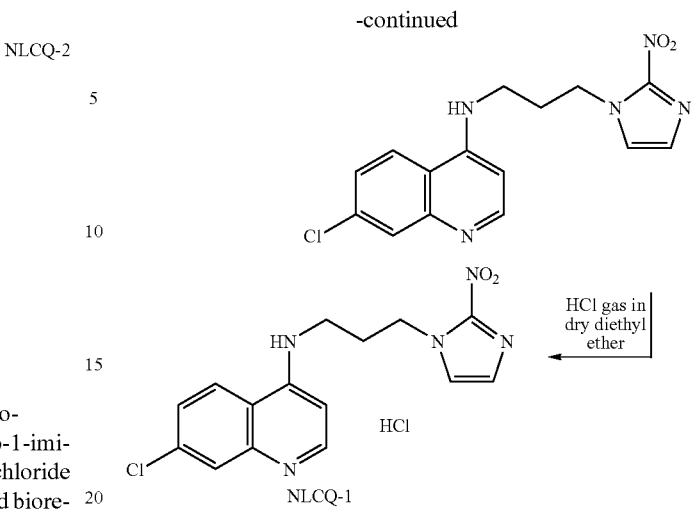

Commercially available 4,7-dichloroquinoline (1) first was converted to the 4-fluoro-derivative (2) by refluxing for 6 hours in DMSO with lyophilized potassium fluoride (KF) (1.5 eq) from a 5% aqueous solution. Then, 4-fluoro-7-chloroquinoline (2) was coupled with 3-(2-nitro-1-imidazolyl) propylamine (3), (1 eq, synthesized in our lab) in propanol, by refluxing for 12 hours (95° C.), to give the free amine of NLCQ-1. The product was purified by preparative TLC (alumina, ethyl acetate with some drops of methanol (MeOH), $R_f$: 0.28, 56% yield) and converted quantitatively to its hydrochloride salt by treating the solution in acetone with hydrogen chloride (HCl) gas in dry diethyl ether. The salt (recrystallized from ethanol/ethyl acetate), an off-white solid, is soluble in water. Stock solutions in water (6 mM) were stable for at least 1 month, at 5° C.

Subsequently, the synthesis was scaled up successfully with slight modifications: A stirred, argon blanketed mixture of 3-(2-nitro-1-imidazolyl)propylamine (3, 2.4 g, 14.1 mmol) and 4-fluoro-7-chloroquinoline (2, 2.7 g, 14.8 mmol) in 1-propanol (250 mL) was heated at 95° C. for 20 hours. The mixture was concentrated to dryness in vacuo and the resulting residue was presorbed over silica gel in MeOH. This was chromatographed on a silica gel column (780 g, 7.5×38 cm) and eluted with EtOAc-MeOH (44:1, 12.5 L). Appropriate fractions as determined by TLC were combined and concentrated in vacuo to yield a foamy solid (4.6 g, 24.1 mmol, 75.2% yield). This solid was gently stirred in MeOH (600 mL), then HCl/MeOH was added (~2.0 M, 44.0 mL). The resultant mixture was concentrated in vacuo to a slurry (~40 mL), diluted with $Et_2O$ (170 mL), and stored at 3° C. for 1 hour. The solids were collected by filtration, then washed with $Et_2O$ (2×5 mL). The crude material was stirred in MeOH (125 mL), concentrated to a volume of 15 mL, filtered, washed with $Et_2O$ (3×15 mL), hexanes (3×10 mL), and dried to constant weight in vacuo to give 8.8 g (80.4%) of purified product (NLCQ-1), mp 244-247° C. (d) (uncorrected). $^1$H NMR (GEN-500, 500 MHz spectrometer) ($D_2O$) δ: 8.27 (d, J=6.6 Hz, 1H), 7.97 (d, J=9.0 Hz, 1H), 7.76 (s, 1H), 7.58 (dd, J=9.0, 2.4 Hz, 1H), 7.52 (s, 1H), 7.12 (s, 1H), 6.73 (d, J=6.6 Hz, 1H), 4.66 (t, J=5.1 Hz, 2H), 3.72 (t, J=5.1 Hz, 2H), 2.40 (m, 2H). HRMS (VG 70-250SE mass spectrometer): Calculated for $C_{15}H_{14}ClN_5O_2$ (free amine): m/z 331.0836. Found: 331.0835. FAB (VG 70-250SE mass spectrometer). Calculated for $C_{15}H_{15}ClN_5O_2$ (M+): m/z 332. Found: 332 (100%).

NLCQ-2 was synthesized similarly to NLCQ-1 by coupling 4-fluoro-7-chloroquinoline (2, 1 eq) with 4-(2-nitro-1-imidazolyl)butylamine (1 eq). The total yield was 47%. The salt was an off white solid, soluble in water. Stock solutions in water (5.6 mM) were stable for at least one month. $^1$H NMR (GEN-500, 500 MHz spectrometer) (D$_2$O) δ: 8.33 (d, J=6.8 Hz, 1H), 8.16 (d, J=9.0 Hz, 1H), 7.92 (s, 1H), 7.71 (d, J=9.0, 1H), 7.53 (s, 1H), 7.17 (s, 1H), 6.80 (d, J=6.8 Hz, 1H), 4.75 (t, J=5.1 Hz, 2H), 3.75 (t, J=4.5 Hz, 2H), 2.12 (m, 2H), 1.91 (m, 2H). HRMS (VG 70-250SE mass spectrometer): Calculated for $C_{16}H_{16}ClN_5O_2$ (free amine): m/z 345.0992. Found: 345.0993. FAB (VG 70-250SE mass spectrometer). Calculated for $C_{16}H_{17}ClN_5O_2$ (M+): m/z 346. Found: 346 (100%).

In the search for new anti-TB drugs, candidate compounds are screened for antibacterial activity. In the standard screening protocol, candidate compounds are screened against *Mycobacterium tuberculosis* H$_{37}$Rv using the Microplate Alamar Blue Assay (MABA). A determination of MIC, which is defined as the lowest concentration causing a reduction in fluorescence (MABA Assay) of 90% relative to controls, is performed. Compounds demonstrating at least 90% inhibition at a concentration of less than 6.25 µg/ml (Minimum Inhibitory Concentration, MIC) are investigated further. Then, a determination of compound toxicity (IC$_{50}$) versus VERO cells at concentrations 62.5 µg/ml or less, or 10× the MIC (MTT assay, 72 hours of exposure), is determined.

Compounds having a Selectivity Index (SI=IC$_{50}$/MIC) of greater than 10 are tested further against *M. tuberculosis* Erdman in monolayers of mouse bone marrow macrophages (Macrophage Assay), against *M. Avium*, and against three strains of singly-drug-resistant (SDR) MTB. Candidate compounds also can be tested as follows:

determination of the Minimum Bacterial Concentration (MBC), which typically is similar to MIC (colony forming assay);

determination of MTD (Minimum Toxic Dose, MTD) in vivo (C57BL/6 female mice, i.p. administration of single doses, 1 week duration); and evaluation in vivo using the standard C57BL/6 model or the GKO (IFN gamma knock out mice) model.

In the in vivo tests, mice are exposed to an aerosol of *M. tuberculosis* Erdman, which deposits approximately 50 bacilli into the lungs of the animal. In both mouse models (GKO or standard C57BL/6), drug treatment begins 20 days after inoculation of the animal with *M. tuberculosis*. Three dose levels of drug are administered (generally i.p. once per day, or orally twice per day). An additional group of mice is administered isoniazid as a positive control. Bacterial counts are measured on day 30 (GKO only) or days 35 and 50 (standard model) in two tissues (lung and spleen), and compared with counts from negative (untreated) controls. Candidate compounds are considered active if they yield at least a 0.75 log 10 reduction in bacterial counts, and moderately active if they afford a lower reduction, (e.g., 0.5 log 10).

More particularly, the 2-nitroimidazolyl-alkylaminoquinolines were tested for MIC against *M. tuberculosis* H$_{37}$Rv in medium and for cytotoxicity against VERO cells.

Compounds are routinely tested for cytotoxicity using VERO cells (C. L. Cantrell et al., *J. Nat. Prod.*, 59:1131-36 (1996); G. C. Mangalindan et al., *Planta Med.*, 66:364-5 (2000)). Compounds are tested against VERO cells at concentrations less than or equal to 1% of the maximum achievable stock concentration. This results in a final DMSO concentration of less than or equal to 1% v/v, which is approximately the maximum noncytotoxic concentration. Testing at very high concentrations allows for the recognition of high degrees of selectivity. Repeat testing is performed for compounds for which the IC$_{50}$ is less than or equal to the lowest tested concentration, when this concentration also is above the MIC for *M. tuberculosis*. After 72 hours exposure, viability is assessed on the basis of cellular conversion of MTT into a soluble formazan product using the Promega CellTiter 96 Aqueous Nonradioactive Cell Proliferation Assay. Rifampin, clarithromycin, capreomycin, isoniazid, minocyclin, and streptomycin are included as controls.

For macrolides having an IC$_{50}$:MIC ratio (i.e., selectivity index SI) greater than 10, cytotoxicity is repeated using the J774.1 macrophage cell line because these are used in the macrophage assay and typically are more sensitive than VERO cells.

Compounds for which the IC$_{50}$:MIC (SI) ratio is greater than 10 are tested for killing of *M. tuberculosis* Erdman (ATCC 35801) in monolayers of J774.1 murine macrophages (EC$_{99}$ and EC$_{90}$; lowest concentration effecting a 90% and 99% reduction in colony forming units at 7 days compared to drug-free controls) at 4-fold or 5-fold concentrations with the lowest concentration just below the MIC.

Assays for demonstrating whole-cell activity (MIC) against *M. tuberculosis* were performed as follows.

MIC/MBC. Compounds were evaluated for MIC vs. *M. tuberculosis* H$_{37}$Rv using the microplate Alamar Blue assay (MABA) described in (L. Collins et al., *Antimicrob. Agents Chemother.*, 41:1004-9 (1997)) except that 7H12 media, rather than 7H9+glycerol+casitone+OADC, is used. The use of this and other redox reagents, such as MTT, have shown excellent correlation with cfu-based (colony forming units) and radiometric analyses of mycobacterial growth. The MIC is defined as the lowest concentration effecting a reduction in fluorescence (or luminescence) of 90% relative to controls. Isoniazid and rifampin are included as positive quality control compounds for each test, with expected MIC ranges of 0.025-0.1 and 0.06-0.125 ug/ml, respectively. MBCs are determined by subculture onto 7H11 agar just prior to addition of Alamar Blue and Tween 80 reagents to the test wells. The MBC is defined as the lowest concentration reducing cfu by 99% relative to the zero time inoculum.

To demonstrate the ability of a 2-nitroimidazolyl-alkylaminoquinoline to control TB bacteria, the following compounds were tested under the TAACF screening program. The four tested compounds were CF3PM, NLCQ-1, NLCQ-2, and NLQZ-1. The structures for NLCQ-1 and NLCQ-2 are provided above. CF3PM and NLQZ-1 have the following structures.

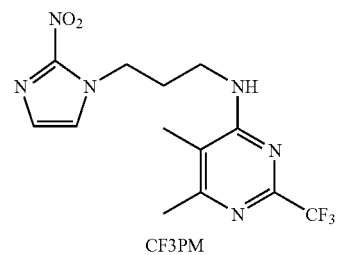

CF3PM

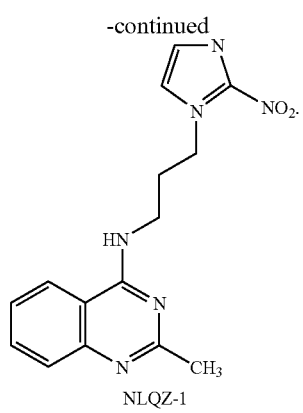

NLQZ-1

The results of the tests are summarized in the following Table 1. The compounds were tested at a pH of 6.7-6.8

TABLE 1

| Compound | % Inh[1] (aerobic) | $H_{37}Rv$ MBC[2] (μg/mL) (hypoxic) |
|---|---|---|
| CF3PM | 23 | 7.01-25 |
| NLCQ-1 | 0 | 3.1 |
| NLCQ-2 | 0 | 6.25 |
| NLQZ-1 | 0 | 12.5-17.4 |

[1]Inh is % inhibition under aerobic conditions at 6.25 μg/mL, only CF3PM showed activity; and
[2]$H_{37}Rv$ MBC is Minimum Bacterial Concentration of a compound that causes ≧99% inhibition in the proliferation of *M. tuberculosis* $H_{37}Rv$ in the clonogenic assay under hypoxic (anaerobic) conditions.

The $H_{37}Rv$ MBC values for the tested compounds were compared to present day anti-TB drugs as positive controls:

| Compound | $H_{37}Rv$ MBC (hypoxic assay) |
|---|---|
| rifampin (RIF) | 2.5 μg/mL |
| isoniazid (INH) | >100 μg/mL |
| minocyclin (MIN) | 156.25 μg/mL |
| streptomycin (SM) | 12.5 μg/mL |
| clarithromycin (CLA) | >312.5 μg/mL |
| capreomycin (CAP) | 37.5 μg/mL |

In this particular hypoxic assay, very few "positive controls" are available. Rifampin is considered an "active" compound, having an MBC of 2.5 μg/mL. Although this value is ten times or more greater than the MBC against log phase *M. tuberculosis*, the value is still within a clinically achievable range (rifampin has a Cmax of 8 μg/mL about two hours after administration of a 600 mg oral dose). Metronidazole has been shown to be active in this assay, but activity is observed only at very high concentrations and the activity is variable. Therefore, metronidazole was not considered as a positive control. The anti-TB drug capreomycin has also been shown to be active, but at a relatively high concentration; i.e., an MBC of 37.5 μg/mL. INH is a classic negative control in this assay, because it is known to be inactive against TB that is not actively dividing. The other control drugs, minocyclin, streptomycin, and clarithromycin were included to provide comparative data, which shows that most drugs are not active in this assay, even at a very high concentration. Table 1 shows that NLCQ-1 and NLCQ-2 have a high activity in this hypoxic assay.

It also was found that NLCQ-1 had a peak plasma concentration of 8.9 μg/mL after an i.p. injection of 10 mg/kg to CD2F1 mice. This dose is only one-third of the MTD of NLCQ-1 (30 mg/kg as a single dose; ≧45 mg/kg as multiple doses). The NLCQ-1 peak plasma concentration of 0.461 μg/mL (29% bioavailability) was achieved after oral administration of 10 mg/kg to CD2F1 mice. An oral MTD was not determined.

NLCQ-1 and NLCQ-2 therefore demonstrate an excellent activity against $H_{37}Rv$. The only other compounds that demonstrate such an activity are rifampins, moxifloxacin, and PA-824.

The following Table 2 contains a summary of results from anti-TB assays in dormant $H_{37}Rv$ cells and toxicity studies in VERO cells.

TABLE 2

| | MBC[1] (μg/mL) | IC₅₀ in VERO cells (μg/mL) | SI[2] |
|---|---|---|---|
| NLCQ-1 | 3.1-18.4 | 146.7 | 8-47.3 |
| NLCQ-2 | 4.9-9.8 | >640 | >65.3-130.6 |
| PA-824[3] | 6.4-12.8 | >640 | >50-100 |
| Rifampin[4] | 2.5 | | |
| Isoniazid | >100 | | |
| Minocyclin | >156.25 | | |
| Streptomycin | >12.5 | | |
| Clarithromycin | >312.5 | | |
| Capreomycin | 37.5 | | |

[1]minimum bactericidal concentration;
[2]selectivity index (IC₅₀/MBC);
[3]a nitroimidazopyran compound currently in a Phase I clinical trial; and
[4]an anti-TB drug known to have activity against dormant bacteria.

In summary, NLCQ-1 and NLCQ-2 were tested with other compounds of the same family against MTB $H_{37}Rv$ under the TAACF umbrella. Both compounds demonstrated activity only in dormant $H_{37}Rv$, with MBC values ranging from 3.1-18.4 μg/ml (NLCQ-1) and 4.9-9.8 μg/ml (NLCQ-2), depending on the assay. In the same test setting, the corresponding MBC for PA-824 ranged from 6.4-12.8 μg/ml. For rifampin, isoniazid, minocyclin, streptomycin, clarithromycin, and capreomycin the corresponding MBC values were 2.5, >100, >156.25, >12.5, >312.5 and 37.5 μg/ml, respectively. Toxicity against VERO cells provided IC₅₀ values of 146.7, >640 and >640 μg/ml for NLCQ-1, NLCQ-2, and PA-824, respectively. Therefore the selectivity index (SI) was 8-47.3, >65.3-130.6, and >50-100 for NLCQ-1, NLCQ-2 and PA-824, respectively.

The following Table 3 contains comparative data for a dormancy assay, using both the colony forming unit (CFU) and luminescence endpoints, which provided similar results. The data shows that NLCQ-1 and NLCQ-2 have about the same activity as PA-824. In fact, NLCQ-2 appears superior to PA-824 in these assays. In this test, dormant $H_{37}Rv$-CA-luxAB strain was used.

TABLE 3

Minimum Bacterial Concentration (MBC)

| | | CFU | | Luciferase | |
|---|---|---|---|---|---|
| Compounds | M.W | MBC (uM) | MBC (μg/mL) | MBC (uM) | MBC (μg/mL) |
| NLCQ-1 | 368 | 50 | 18.4 | 25 | 9.2 |
| NLZQ-1 | 348.5 | 50 | 17.43 | 50 | 17.43 |
| CF3PM | 280.5 | 50 | 14.03 | 25 | 7.01 |
| NLCQ-2 | 392 | 25 | 9.80 | 12.5 | 4.9 |

TABLE 3-continued

Minimum Bacterial Concentration (MBC)

| Compounds | M.W | CFU | | Luciferase | |
| --- | --- | --- | --- | --- | --- |
| | | MBC (uM) | MBC (µg/mL) | MBC (uM) | MBC (µg/mL) |
| PA-824 | 359 | 35.65 | 12.8 | 17.82 | 6.4 |
| RIF | 822.96 | 4.86 | 4 | 4.86 | 4 |
| INH | 137.14 | 145.84 | 20 | 583.35 | 80 |

FIG. 1 is a bar graph showing the percent inhibition of a TB enzymatic system that forms an essential TB cell wall component. In FIG. 1, control (no compound) and two positive control (minus dTDP, minus glucose; and TDP, an inhibitor) are included. All compounds were tested at a concentration of 10 µM, i.e., 2.8-3.9 µg/mL. The bar graph shows that NLCQ-1 and NLCQ-2 demonstrate a greater than 50% inhibition, further illustrating the anti-TB capabilities of the 2-nitroimidazolyl-alkylaminoquinolines.

In an enzyme assay, 52.8% and 49.1% inhibition was demonstrated by NLCQ-1 and NLCQ-2, respectively at 10 µM concentration (3.68 µg/ml and 3.92 µg/ml for NLCQ-1 and NLCQ-2, respectively), under normoxic conditions. This enzymatic system (RmlB, RmlC, and RmlD) is responsible for the synthesis of rhamnose, a necessary sugar for the synthesis of the bacterial cell wall (Ma et al., *Antimicrobial Agents and Chemotherapy*, (45) 5:1407-16 (2001)).

The above data shows that weak DNA-intercalating 2-nitroimidazolyl-alkylaminoquinolines, and particularly NLCQ-1 and NLCQ-2, are active against dormant $H_{37}Rv$ *M. tuberculosis* bacteria under hypoxic conditions. Furthermore, toxicity tests against VERO cells provided selectivity indices of 47.3 and greater than 130.6 for NLCQ-1 and NLCQ-2, respectively. The 2-nitroimidazolyl-alkylaminoquinolines therefore are capable of targeting latent TB forms with an ability to shorten the duration of an anti-TB regimen or the number of doses required for an anti-TB treatment. The 2-nitroimidazolyl-alkylaminoquinolines can be used alone, or in combination with drugs that target active TB bacteria, in the treatment of latent TB, active TB, and MDR TB.

NLCQ-1 and NLCQ-2 also are significantly more potent (on a concentration basis) than metronidazole as hypoxia selective cytotoxins. In addition, NLCQ-1 and NLCQ-2 exhibit similar MBC values against dormant TB bacteria, and similar selectivity indices with the nitroimidazopyran PA-824. In fact, NLCQ-2 appears superior to PA-824 (see Table 3). Also, the NLCQ-1 and NLCQ-2 compounds are more hydrophilic (i.e., greater aqueous solubility) than PA-824.

In addition, NLCQ-1 exhibits good stability in human plasma, fast tissue penetration, and favorable pharmacokinetics in mice and dogs. Furthermore, the mouse data suggest that oral administration of NLCQ-1 may achieve plasma concentration and systemic exposure similar to those observed after i.v. administration (*Cancer Chem. Pharmacol.* 51:483-487 (2003)). The excellent recovery of NLCQ-1 from biological fluids has been established. Toxicity studies for NLCQ-1 in mice, rats, and dogs showed no adverse effects after an i.v. daily administration of 16 mg/kg (female rats) and 10.95 mg/kg (dogs) and an i.p. administration of 30 mg/kg (bolus dose) or 45 mg/kg as 3 fractions of 15 mg/kg (given every two hours daily) in mice.

The 2-nitroimidazolyl-alkylaminoquinolines can be formulated to provide a pharmaceutical composition useful in a method of treating TB. A 2-nitroimidazolyl-alkylaminoquinoline active agent, or a mixture of these active agents, typically is present in such a pharmaceutical composition in an amount of about 0.1% to about 75%, by weight.

Pharmaceutical compositions containing a 2-nitroimidazolyl-alkylaminoquinoline, i.e., an active agent, are suitable for administration to humans or other mammals. Typically, the pharmaceutical compositions are sterile, and contain no toxic, carcinogenic, or mutagenic compound which would cause an adverse reaction when administered.

A pharmaceutical composition containing an active agent, or mixture of active agents can be administered by any suitable route, for example by oral, buccal, inhalation, sublingual, rectal, vaginal, intracisternal through lumbar puncture, transurethral, nasal, or parenteral (including intravenous, intramuscular, subcutaneous, and intracoronary) administration. A pharmaceutical composition containing the 2-nitroimidazolyl-alkylaminoquinoline, or a mixture thereof, preferably is administered by an oral or parenteral route. Parenteral administration can be accomplished using a needle and syringe. Implant pellets also can be used to administer an active agent parenterally. The active agents also can be administered as a component of an ophthalmic drug-delivery system.

The pharmaceutical compositions are administered in an effective amount to achieve its intended purpose. More specifically, a "therapeutically-effective amount" means an amount effective to treat TB, and particularly latent TB. Determination of a therapeutically-effective amount is well within the capability of those skilled in the art, especially in light of the detailed disclosure provided herein.

The exact formulation, route of administration, and dosage is determined by an individual physician in view of the patient's condition. Dosage amount and interval can be adjusted individually to provide levels of the active agents that are sufficient to maintain therapeutic effects.

The amount of pharmaceutical composition administered is dependent on the individual being treated, on the individual's weight, the severity of the affliction, the manner of administration, and the judgment of the prescribing physician.

Specifically, for administration to a human in the curative treatment of a disease, oral dosages of an active agent is about 10 to about 500 mg daily for an average adult patient (70 kg). Thus, for a typical adult patient, individual doses contain about 0.1 to about 500 mg active agent, in a suitable pharmaceutically acceptable vehicle or carrier, for administration in single or multiple doses, once or several times per day. Dosages for intravenous, buccal, or sublingual administration typically are about 0.1 to about 10 mg/kg per single dose as required. In practice, the physician determines the actual dosing regimen that is most suitable for an individual patient, and the dosage varies with the age, weight, and response of the particular patient. The above dosages are exemplary of the average case, but there can be individual instances in which higher or lower dosages are merited, and such are within the scope of this invention.

An active agent can be administered alone, or in admixture with a pharmaceutical carrier selected with regard to the intended route of administration and standard pharmaceutical practice. Pharmaceutical compositions for use in accordance with the present invention, including ophthalmic preparations, thus can be formulated in a conventional manner using one or more physiologically acceptable carriers comprising excipients and auxiliaries that facilitate processing of an active agent into preparations that can be used pharmaceutically.

These pharmaceutical compositions can be manufactured in a conventional manner, e.g., by conventional mixing, dissolving, granulating, dragee-making, emulsifying, or lyophilizing processes. Proper formulation is dependent upon the route of administration chosen. When a therapeutically-effective amount of an active agent is administered orally, the formulation typically is in the form of a tablet, capsule, powder, solution, or elixir. When administered in tablet form, the pharmaceutical composition additionally can contain a solid carrier, such as a gelatin or an adjuvant. The tablet, capsule, and powder contain about 5% to about 95%, preferably about 25% to about 90%, of an active agent of the present invention. When administered in liquid form, a liquid carrier, such as water, petroleum, or oils of animal or plant origin, can be added. The liquid form of the pharmaceutical composition can further contain physiological saline solution, dextrose or other saccharide solutions, or glycols. When administered in liquid form, the pharmaceutical composition contains about 0.5% to about 90%, by weight, of an active agent, and preferably about 1% to about 50%, by weight, of an active agent.

When a therapeutically-effective amount of an active agent is administered by intravenous, cutaneous, or subcutaneous injection, the composition is in the form of a pyrogen-free, parenterally acceptable aqueous preparation. The preparation of such parenterally acceptable solutions, having due regard to pH, isotonicity, stability, and the like, is within skill in the art. A preferred composition for intravenous, cutaneous, or subcutaneous injection typically contains an isotonic vehicle in addition to an active agent of the present invention.

An active agent can be readily combined with pharmaceutically acceptable carriers well-known in the art. Such carriers enable the active agent to be formulated as tablets, pills, dragees, capsules, liquids, gels, syrups, slurries, suspensions and the like, for oral ingestion by a patient to be treated. Pharmaceutical compositions for oral use can be obtained by adding the active agent with a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

An active agent can be formulated for parenteral administration by injection, e.g., by bolus injection or continuous infusion. Compositions for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous dispersions of the active agent. Additionally, suspensions of the active agent can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the dispersibility of the compounds and allow for the preparation of highly concentrated compositions. Alternatively, a present pharmaceutical composition can be in powder form for constitution with a suitable vehicle, e.g., sterile pyrogen-free water, before use.

An active agent also can be formulated in rectal compositions, such as suppositories or retention enemas, e.g., containing conventional suppository bases. In addition to the preparations described previously, an active agent also can be formulated as a depot preparation. Such long-acting preparations can be administered by implantation (for example, subcutaneously or intramuscularly) or by intramuscular injection. Thus, for example, an active agent can be formulated with suitable polymeric or hydrophobic materials (for example, as an emulsion in an acceptable oil) or ion exchange resins.

In particular, an active agent can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid compositions can be prepared with pharmaceutically acceptable additives, such as suspending agents. A composition also can be injected parenterally, for example, intravenously, intramuscularly, subcutaneously, or intracoronarily. For parenteral administration, the composition is best used in the form of a sterile aqueous solution which can contain other substances, for example, salts, or monosaccharides, such as mannitol or glucose, to make the solution isotonic with blood.

The present invention, therefore, discloses the use of a 2-nitroimidazolyl-alkylaminoquinoline, or mixtures thereof, for the oral, parenteral, sublingual, rectal, vaginal, or urethral treatment of TB. The method comprises administering a therapeutically-effective amount of a pharmaceutical preparation comprising an active agent.

The pharmaceutical preparation also can contain a second anti-TB drug, or the 2-nitroimidazolyl-alkylaminoquinoline can be coadministered with one or more additional anti-TB drug to provide a treatment against latent TB, active TB, and MDR TB. Suitable anti-TB drugs for coadministration with a 2-nitroimidazolyl-alkylaminoquinoline include, but are not limited to, isoniazid, rifampin, pyrazinamide, streptomycin, minocylcin, clarithromycin, capreomycin, cethromycin, telithromycin, moxifloxacin, PA-824, and metronidazole. Additional anti-TB drugs, such as carboxylates, quinolones, macrolides, InhA inhibitors, isocitrate lyase inhibitors, pleuromutilins, and nitro-imidazole-oxazoles also can be coadministered with a 2-nitroimidazolyl-alkylaminoquinoline of the present invention.

Modifications and variations of the invention as hereinbefore set forth can be made without departing from the spirit and scope thereof, and only such limitations should be imposed as are indicated by the appended claims.

What is claimed is:

1. A method of treating tuberculosis comprising administering a therapeutically-effective amount of a 2-nitroimidazolyl-alkylaminoquinoline, or a pharmaceutically acceptable salt thereof, to an individual in need thereof, wherein the 2-nitroimidazolyl-alkylaminoquinoline is defined by a structural formula

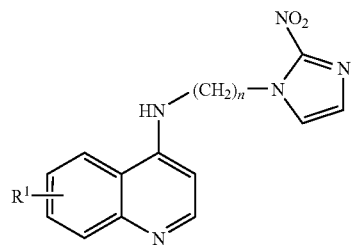

wherein $R^1$ is present at the 6, 7, or 8 position of the quinoline ring and is selected from the group consisting of halo, methyl, methoxy, and trifluromethyl, and n is an integer 2 through 6.

2. The method of claim 1 wherein R¹ is halo.

3. The method of claim 1 wherein n is 3 or 4.

4. The method of claim 1 wherein the 2-nitroimidazolyl-alkylaminoquinoline is selected from the group consisting of

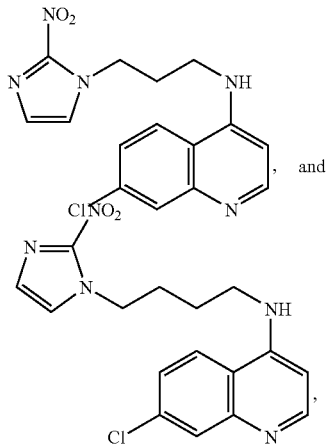

or a mixture thereof.

5. The method of claim 1 wherein the tuberculosis is latent tuberculosis, active tuberculosis, or multidrug-resistant tuberculosis.

6. The method of claim 1 wherein the tuberculosis is latent tuberculosis.

7. The method of claim 6 further comprising administering a therapeutically-effective amount of a second drug useful in a treatment of tuberculosis, wherein the second drug is selected from the group consisting of isoniazid, rifampin, pyrazinamide, streptomycin, minocyclin, clarithromycin, capreomycin, cethromycin, telithromycin, PA-824, metronidazole, and moxifloxacin, or mixtures thereof.

8. The method of claim 7 wherein the 2-nitroimidazolyl-alkylaminoquinoline and the second drug are administered simultaneously.

9. The method of claim 7 wherein the 2-nitroimidazolyl-alkylaminoquinoline and the second drug are administered sequentially.

* * * * *